United States Patent [19]

Morris

[11] Patent Number: 5,775,336
[45] Date of Patent: Jul. 7, 1998

[54] TUBULAR MEDICAL DEVICE

[75] Inventor: Michael S. Morris, North Potomac, Md.

[73] Assignee: Georgetown University, Washington, D.C.

[21] Appl. No.: 655,808

[22] Filed: May 31, 1996

[51] Int. Cl.$^6$ ............................................. A61F 11/00
[52] U.S. Cl. ................................ 128/857; 128/864
[58] Field of Search .......................... 128/846, 864, 128/865, 866, 867, 868, 857; 2/2

[56] References Cited

U.S. PATENT DOCUMENTS

| | | | |
|---|---|---|---|
| 2,427,664 | 9/1947 | Dunbar | 128/867 |
| 2,573,923 | 11/1951 | Mazz | 128/864 |
| 2,804,072 | 8/1957 | Genzer | 128/864 |
| 4,353,364 | 10/1982 | Woods | 128/867 |
| 4,896,679 | 1/1990 | St. Pierre | 128/865 |

*Primary Examiner*—Michael A. Brown
*Attorney, Agent, or Firm*—Oliff & Berridge PLC

[57] ABSTRACT

A tubular medical device is adapted for placement into a human patient or other living being. The tubular medical device includes a body member and a rib structure. The body member extends along a longitudinal axis and has an outer surface and an inner surface. The inner surface defines a hole extending Longitudinally through the body member between opposite ends thereof. The rib structure is connected to the outer surface of the body member and projects outwardly from the outer surface relative to the longitudinal axis. The rib structure and the outer surface of the body member define at least one channel oriented transversely to the longitudinal axis. The tubular medical device can be constructed in a variety of embodiments including a tympanostomy tube device, a ribbed sleeve and an elongated tube.

16 Claims, 4 Drawing Sheets

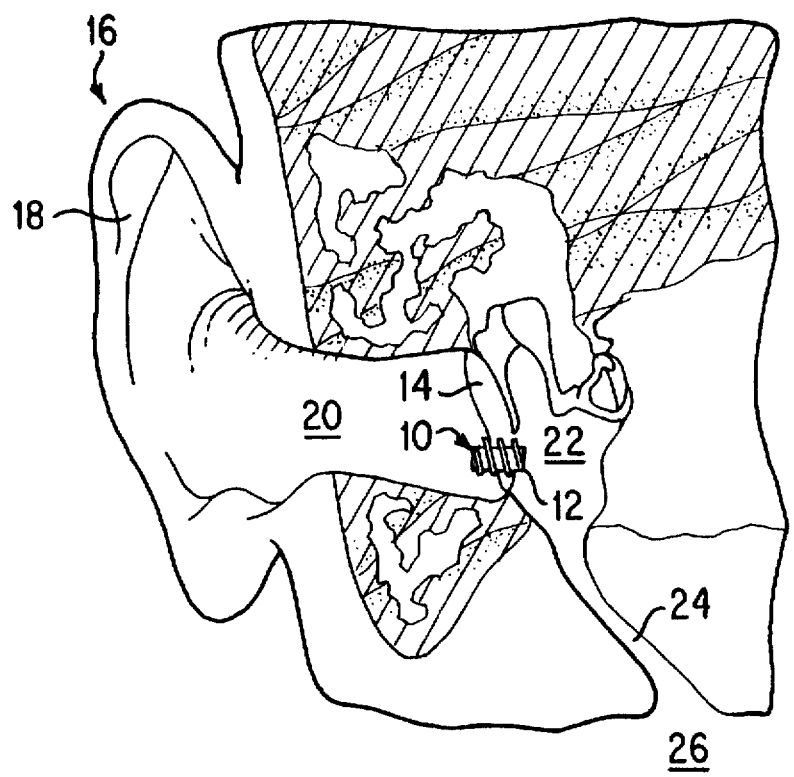
FIG. 1
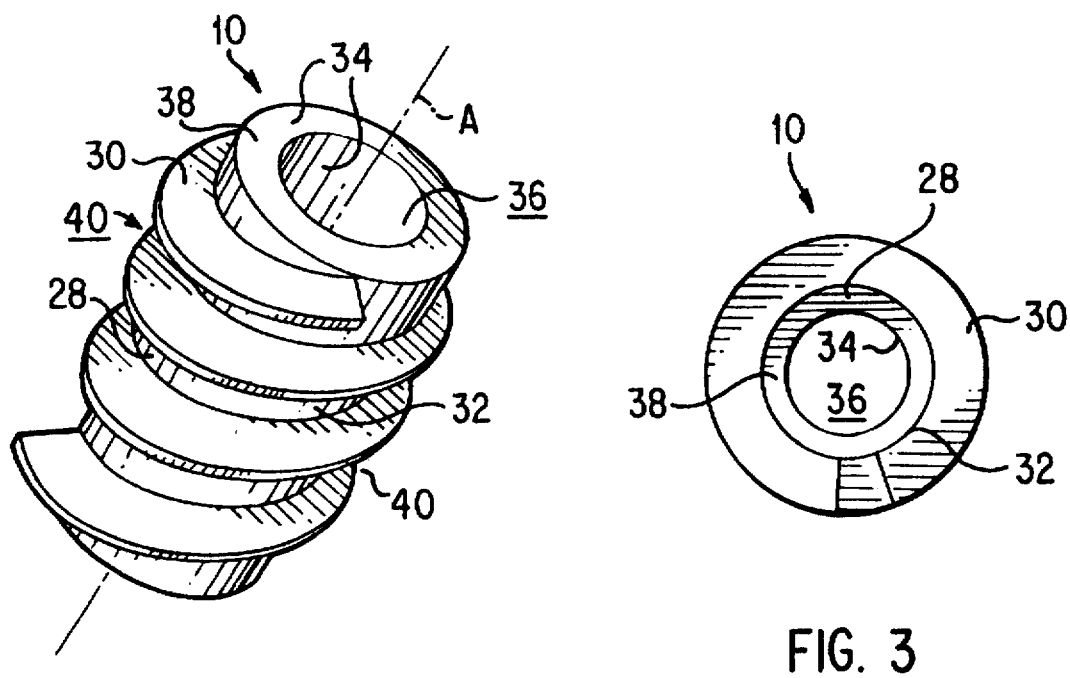
FIG. 2
FIG. 3

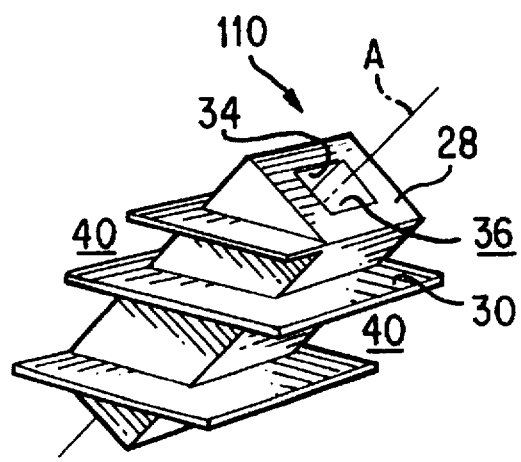
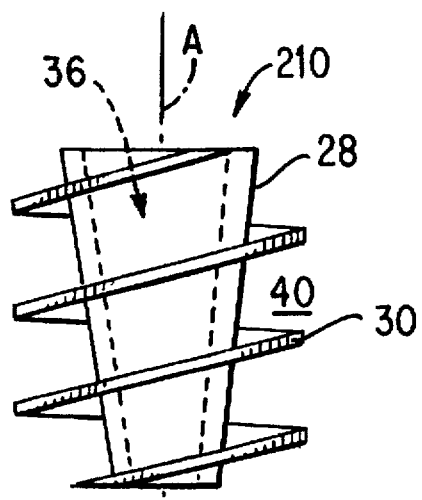
FIG. 6     FIG. 7
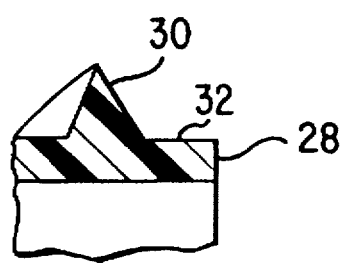
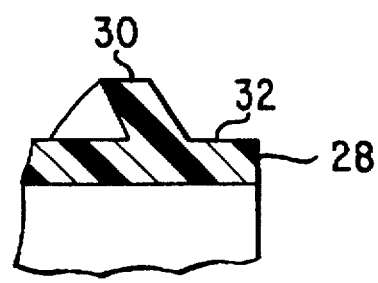
FIG. 8     FIG. 9
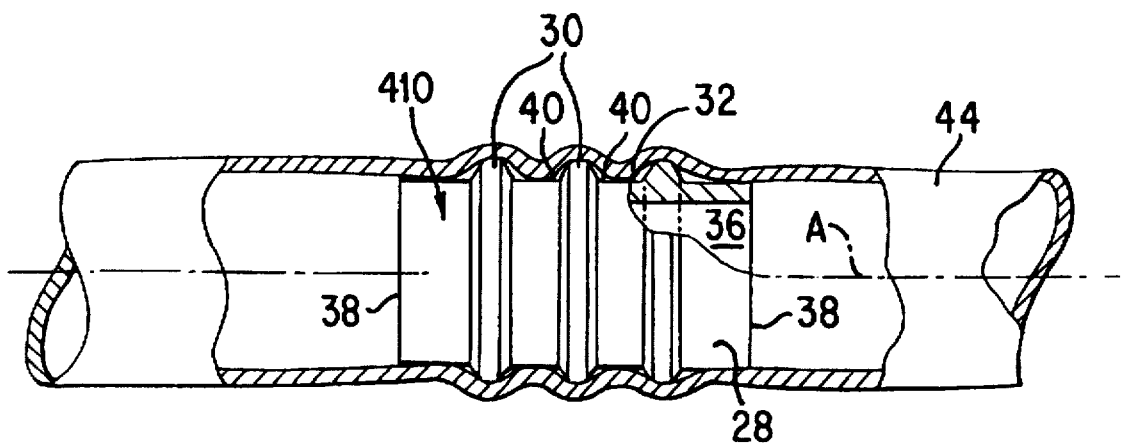
FIG. 10

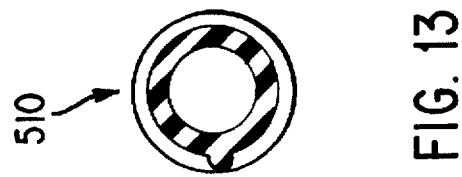
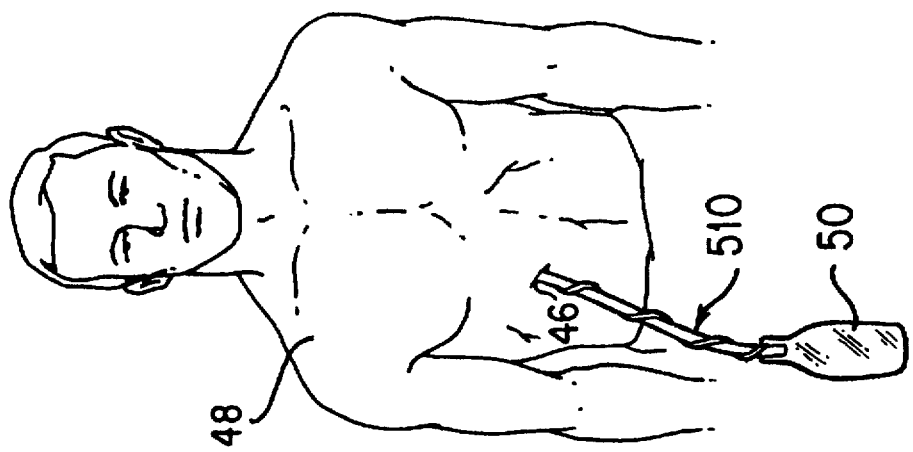
FIG. 13
FIG. 12
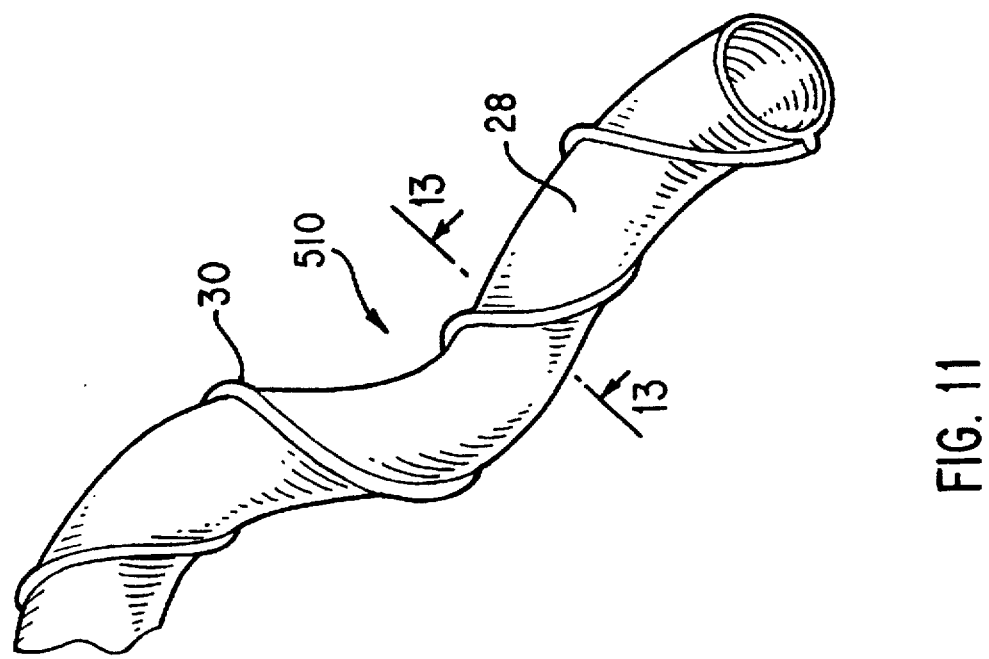
FIG. 11

TUBULAR MEDICAL DEVICE

BACKGROUND OF THE INVENTION

1. Field of the Invention

The present invention relates to a tubular medical device which is adapted for placement into a living being. More particularly, the present invention is directed to a tympanostomy tube device which is adapted for insertion into and temporary retention in an orifice formed in an eardrum of an ear of a living being.

2. Description of Related Art

Ear infection, more popularly known in the medical field as "otitis media", is a common ailment that inflicts many individuals throughout the world. An ear infection typically occurs when the eustachian tube which connects the middle ear cavity with the nasopharynx becomes blocked. This blockage prevents fresh air from circulating within the middle ear cavity. This lack of air circulation renders the middle ear cavity a breeding ground for viruses and bacteria which cause infection.

Children between the ages of six months and five years are particularly susceptible to ear infection for two reasons. One, at such a young age, the eustachian tube is rather short and therefore viruses and bacteria entering into the middle ear cavity from the eustachian tube do not have a very long distance to travel. Two, the eustachian tube in a child is oriented generally horizontally as opposed to its orientation in an adult which is disposed angularly downwardly from the middle ear cavity to the nasopharynx. Thus, the downwardly disposed eustachian tube of an adult facilitates drainage from the middle ear cavity.

Usually, ear infections are first treated with medicine. Sometimes, medicinal treatment fails and, as a result, a surgical procedure, commonly referred to in the medical industry as a "tympanostomy", must be performed. This surgical procedure requires the patient to be anesthetized so that an orifice can be made into the tympanic membrane, commonly referred to as the "eardrum", so that a tympanostomy tube can be inserted therein. The tympanostomy tube includes a hole extending therethrough so that atmospheric air in the auditory channel of the ear can enter into, circulate, and exit from the middle ear cavity of the patient. In essence, the tympanostomy tube is a by-pass for the blocked eustachian tube. Typically, allowing air to ventilate throughout the middle ear cavity cures ear infection.

Many types of tympanostomy tubes have been used for curing ear infection. One type of tympanostomy tube is a cylindrically-shaped tube. Unfortunately, because of epithelial cellular movement of the eardrum, a cylindrically-shaped tube with a smooth outer surface can be easily extruded from the orifice. As a result, another surgical procedure is required to re-insert the cylindrical tympanostomy tube. To alleviate this problem of extrusion, manufacturers have designed a smooth cylindrical tube having annular flanges attached at opposite ends. These flanges retain the smooth cylindrical tube within the orifice. However, to remove the tympanostomy tube, another surgical procedure is required.

Also, other types of tubular medical devices are often used in the health care profession that are placed into patients either temporarily or permanently. One example of a temporary tubular medical device is a drainage tube that is inserted through an incision between the ribs of a sickly patient in order to drain fluid that has accumulated within the thoracic cavity outside of the lungs. It is quite common that such a drainage tube has a smooth outer surface for easily inserting into and removing from the thoracic cavity. Sometimes, an active patient may accidentally cause the smooth tubular medical device to become extruded from the incision. An example of a permanent placement of a tubular medical device in the health care industry is a sleeve that is surgically implanted into a blood vessel to support a weakened blood vessel wall from collapsing. Often, such sleeves have a smooth outer surface which can tend to slide within the blood vessel when the patient is exceptionally active.

OBJECTS AND SUMMARY OF THE INVENTION

There is a need in the medical industry to provide new and improved tubular medical devices that resist movement after being placed into a human patient or other living being. There is another need in the industry to provide tubular medical devices such as tympanostomy tubes which are resistant yet susceptible to extrusion from an orifice formed in the eardrum of an ear. It would be advantageous to have tubular medical devices that are resistant to extrusion so that ambulatory patients could be more physically active. It would also be advantageous if such tubular medical devices could be placed either temporarily or permanently into human patient or other living beings.

It is an object of the present invention to provide a tympanostomy tube device which can be inserted into and temporarily retained in an orifice formed in an eardrum of an ear of a patient so that atmospheric air can be ventilated between a middle ear cavity and an auditory canal of the ear.

It is another object of the present invention to provide a tympanostomy tube device that is resistant to extrusion yet susceptible to extrusion so that, in the long term, the tympanostomy tube device can be extruded by epithelial cellular movement of the eardrum without intervention by a physician.

Yet another object of the invention is to provide a tubular medical device that is resistant to extrusion so that ambulatory patients can be more physically active without fear of accidentally extruding the tubular medical device from placement inside a patient's body.

Accordingly, a tubular medical device and, particularly, a tympanostomy tube device, are hereinafter described. In its broadest form, the tubular medical device and the tympancostomy tube device include a body member and a rib structure. The body member extends along a longitudinal axis and includes an outer surface and an inner surface. The inner surface defines a hole extending longitudinally through the body member between a pair of opposite ends of the body member. The rib structure is connected to the outer surface of the body member and projects outwardly from the outer surface relative to the longitudinal axis. The rib structure and the outer surface of the body member define at least one channel which is oriented transversely to the longitudinal axis.

It is preferred that the rib structure is a helix that extends to and between the opposite ends of the body member. Alternatively, the rib structure is a plurality of rib elements. Each of the rib elements extend circumferentially around the outer surface of the body member. The plurality of rib elements are disposed away from and between the opposite ends of the body member.

Preferably, the body member is configured in a shape of a cylindrical tube. It is also preferred that the body member and the rib structure are manufactured as a unitary construction. The body member and the rib structure can be fabricated from either a stiff yet resilient material such as rubber, plastic, silicone and polyethylene or from a rigid material such as stainless steel and titanium.

BRIEF DESCRIPTION OF THE DRAWINGS

These and other objects of the present invention will become more readily appreciated and understood from a consideration of the following detailed description of the exemplary embodiments of the present invention when taken together with the accompanying drawings, in which:

FIG. 1 is a partial schematic view partially in cross-section of an ear structure of a human head with a first embodiment of a tubular medical device of the present invention in a form of a tympanostomy tube device that is inserted in an eardrum;

FIG. 2 is a perspective view of the tympanostomy tube device of the present invention shown in FIG. 1;

FIG. 3 is a top and a bottom plan view of the tympanostomy tube device of the present invention shown in FIGS. 1 and 2;

FIG. 6 is a perspective view of a second embodiment of the tubular medical device of the present invention in the form of a tympanostomy tube device;

FIG. 7 is a side view in elevation of a third embodiment of the tubular medical device of the present invention in the form of a. tympanostomy tube device;

FIG. 8 is a partial side view in cross-section illustrating a triangular configuration of a rib structure of the present invention;

FIG. 9 is a partial side view in cross-section illustrating a rhomboidal cross-section of the rib structure of the present invention;

FIG. 10 is a side view in elevation and partially broken away of a fourth embodiment of the tubular medical device of the present invention in a form of a ribbed sleeve;

FIG. 11 is a perspective view of a fifth embodiment of a tubular medical device of the present invention in a form of an elongated tube;

FIG. 12 is a front elevational view of the fifth embodiment of the tubular medical device shown in FIG. 11 with one end inserted into a thoracic cavity of a patient while another end is inserted into a container; and FIG. 13 is a cross-sectional view of the elongated tube taken along lines 3-13 of FIG. 11.

DETAILED DESCRIPTION OF THE PREFERRED EMBODIMENTS

A tubular medical device of the present invention is adapted for placement into a human patient or other living being. One of ordinary skill in the art would appreciate that the tubular medical device of the present invention can be a shortened tube such as a tympanostomy tube device or a bushing for supporting a weakened or collapsed portion of a blood vessel or an elongated tube such as for draining fluid accumulating inside a human patient or other living being. In any application, the tubular medical device of the present invention is constructed to resist yet be susceptible to extrusion from an orifice within which the tubular medical device of the present invention is placed.

Figure 4:
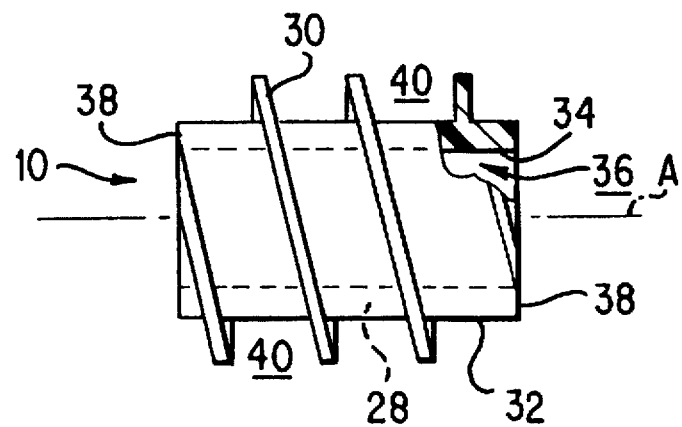
FIG. 4 is a side view in elevation partially broken away of the tympanoEtomy tube device of the present invention shown in FIGS. 1 and 2.

A first embodiment of a shortened tubular medical device of the present invention in a form of a tympanostomy tube device 10 is generally introduced in FIGS. 1–5B. With reference to FIG. 1, tympanostomy tube device 10 is inserted into an orifice 12 of an eardrum 14, otherwise known in the medical industry as a tympanic membrane, of an ear structure 16. FIG. 1 illustrates ear structure 1L6 of a human being although one of ordinary skill in the art would appreciate that such ear structure can be for other living beings. Ear structure 16 includes an ear 18, an auditory canal 20 and a middle ear cavity 22 with, eardrum 14 providing a barrier between auditory canal 20 and middle ear cavity 22. Tympanostomy tube device 10 is adapted for insertion into and temporary retention in orifice 12 formed in eardrum 14 to provide fluid communication between middle ear cavity 22 and auditory canal 20. A eustachian tube 24 interconnects middle ear Cavity 22 and a nasopharynx 26. In FIGS. 2–4, tympanostomy tube device 10 includes a body member 28 and a rib structure 30. Body member 28 extends along a longitudinal axis "A" and has an outer surface 32 and an inner surface of 34. Inner surface 34 defines a hole 36 which extends longitudinally through body member 28 and between opposite ends 38 of body member 28.

Rib structure 30 is connected to outer surface 32 of body member 28 and projects outwardly from outer surface 32 relative to longitudinal axis "A", preferably in a radial direction. Rib structure 30 and outer surface 32 of body member 28 define a channel 40 which is oriented transversely to longitudinal axis "A". Although not by way of limitation, body member 28 and rib structure 30 are a unitary construction.

For the first embodiment of the tympanostomy tube device 10 of the present invention, rib structure 30 is a helix which extends from and between opposite ends 38 of body member 28. As best shown in FIG. 4, rib structure 30 is configured in cross-section in a shape of a rectangle, although other shapes, such as ones discussed below, can be used. As shown in FIGS. 2 and 3, body member 28 is configured as a cylindrically-shaped tube having an annular cross-section.

It is preferred that the tympanostomy tube device 10 of the present invention is fabricated from a stiff yet resilient material such as rubber, plastic, silicone and polyethylene. However, tympanostomy tube 10 of the present invention can be fabricated from a rigid material such as stainless steel or titanium. It is further possible that body member 28 and rib structure 30 are fabricated from either the same material or different materials.

Figure 5A:
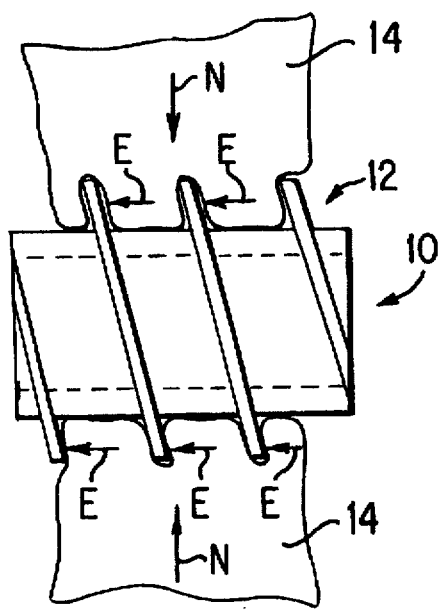
FIG. 5A is an enlarged side view in elevation of the tympanostomy tube device inserted in an orifice of the eardrum illustrating, in theory, epithelial cellular movement of the eardrum which, in turn, creates extrusion forces.
Figure 5B:
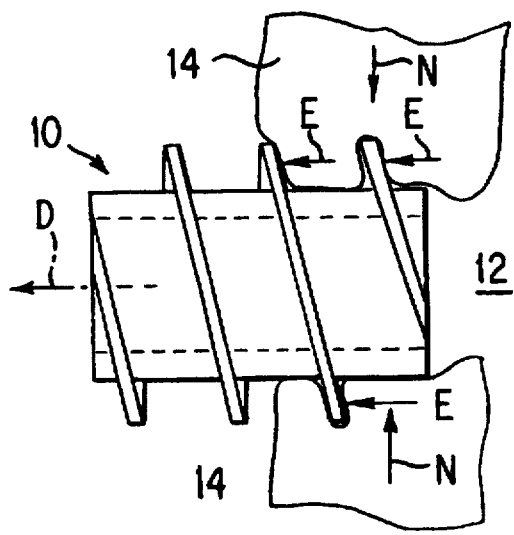
FIG. 5B is an enlarged side view in elevation of the tympanostomy tube device inserted in the orifice of the eardrum illustrating Espithelial cell movement of the eardrum which, in turn, creates extrusion forces causing the tympanostomy tube device to be extruded therefrom.

It is well known in the medical industry that natural forces are constantly working in the eardrum for the primary purpose of expelling debris such as dead cells and dust for the purpose of: maintaining cleanliness of the ear structure. This is due, at least in part, to epithelial cellular movement of the eardrum. As best shown in FIG. 5A and B these natural forces are represented by arrows "N". It is theorized that natural forces "N" generate extrusion forces represented by arrows "E" which tend to extrude tympanostomy tube device 10 over a period of time from orifice 12 of eardrum 14. FIG. 5A illustrates tympanostomy tube device 10 in its original position as it was inserted initially with natural forces "N" and extrusion forces "E" acting on tympanostomy tube device 10. FIG. 5B illustrates tympanostomy tube device 10 being extruded from orifice 12 as a result of extrusion forces "E" in a direction shown by arrow "D" over a period of time from when tympanostomy tube device 10 was originally inserted. Thus, these natural forces will cause tympanostomy tube device 10 of the present invention to be extruded from the eardrum over a period of time. This is desirable for two primary reasons. One, physician intervention is no longer required to extract tympanostomy tube device 10 which, in turn, saves physician time and patient cost. Second, the patient wearing tympanostomy tube device 10 avoids being anesthetized for removal of tympanostomy tube device 10 thereby eliminating any risk associated with anesthesia.

A second embodiment of the tympanostomy tube device 110 is illustrated in FIG. 6. Body member 28 is configured in a form of a rectangularly-shaped tube and rib structure 30 is a helix forming channel 40 which spirals about body member 28 in a general direction of longitudinal axis "A". Inner surface 34 defines hole 36 having a rectangular shape.

A third embodiment of a tympanostomy tube device 210 of the present invention is illustrated in FIG. 7. Body member 28 is a frustoconically-shaped tube having a frustoconically-shaped hole 36 extending therethrough. Rib structure 30 forms a continuous channel 40 that spirals about body member 28 in a general direction of longitudinal axis "A".

By way of example, alternate cross-sectional configurations of rib structure 30 are shown in FIGS. 8 and 9. FIG. 8 shows a triangularly-shaped rib structure 30. FIG. 9 illustrates a rhomboidally-shaped cross-section.

One of ordinary skill in the art would appreciate that the tympanostomy tube device can be fabricated in a variety of sizes, shapes and dimensional specifications. A skill artisan, for example, may change the rib structure in a manner to provide more "threads per inch," a conventional term commonly known among those familiar with machine screws. More "threads per inch" might tend to make extrusion by epithelial cellular movement of the eardrum more difficult which, in turn, would require a longer time period for extrusion. This is a desirable feature because now a physician can match the appropriately designed tyrapanostomy tube device to the patient based upon an estimated time period most suitable for wearing it.

A fourth embodiment, of a tubular medical device in a form of a bushing structure 410 is illustrated in FIG. 10. Bushing structure 410 includes body member 28 and rib structure 30. Rib structure 30 is a plurality of rib elements 42 which are disposed apart from and between opposite ends 38 of body member 28. Each of rib elements 42 project radially from outer surface 32 of body member 28 relative to longitudinal axis "A" and extend circumferentially around outer surface 32 of body member 28. Sequential ones of rib elements 42 disposed apart from each other and along with outer surface 32 of body member 28 define channels 40 therebetween, which also extends circumferentially about body member 28. By way of example only and not by way of limitation, the purpose of bushing structure 410 is to support a weakened or collapsed wall of a blood vessel 44 as would easily be understood by a skilled artisan. For the fourth exemplary embodiment of bushing structure 410 of the present invention, the cross-sectional shape of each rib element 42 is frustoconical.

A fifth embodiment of a tubular medical device in a form of an elongated tube 510 is generally introduced in FIGS. 11–13. Elongated tube 510 includes body member 28 and rib structure 30 which is a helix. As shown in FIG. 12, one end of elongated tube 510 is inserted into an incision 46 of a patient 48 while an opposite end of elongated tube 510 is inserted into a container 50. Although not by way of limitation, elongated tube 510 provides a conduit for a fluid accumulating within patient 48 to drain into container 50. Rib structure 30 provides resistance of elongated tube 510 from being extruded from incision 46. Therefore, patient 48 can be more active without fear that elongated tube 510 would become accidentally extruded from incision 46. Even though elongated tube 510 is resistant to extrusion, it is susceptible of being removed from incision 46. As shown in FIG. 13, rib structure 30 has a domal cross-section.

A skilled artisan would appreciate that the tubular medical device of the present invention simultaneously provides resistance but susceptibility to extrusion. The tubular medical device of the present invention can be used to drain a liquid from a patient or provide ventilation of atmospheric air to a cavity such as the middle ear cavity as discussed above. However, the skilled artisan would not consider the rib structure of this invention as analogous to a machined thread on a screw or bolt because the rib structure must allow for extrusion and for interaction with pliable living tissue.

Accordingly, the present invention has been described with particularity directly to the embodiments of the present invention. It should be appreciated, though, that the present invention is defined by the following claims so that modifications or changes may be made to the embodiments of the present invention without departing from the inventive concepts contained herein.

What is claimed is:

1. A tubular medical device adapted for placement into an orifice formed in an eardrum of an ear structure of a living being, comprising:

a body member extending along a longitudinal axis and having an outer surface and an inner surface, said inner surface defining a hole extending longitudinally through said body member between opposite end is of said body member; and a rib structure connected to said outer surface of said body member and projecting outwardly from said outer surface relative to the longitudinal axis in a manner whereby said rib structure and said outer surface define at least one channel oriented transversely to the longitudinal axis and spiralling about said body member in a general direction of the longitudinal axis wherein said body member and said rib structure being sized to be received by the orifice formed in the eardrum.

2. A tubular medical device according to claim 1, wherein said rib structure is a helix.

3. A tubular medical device according to claim 2, wherein said helix extends from and between said opposite ends.

4. A tubular medical device according to claim 1, wherein said body member is configured in cross-section in a shape selected from a group including annular and rectangular.

5. A tubular medical device according to claim 1, wherein said rib structure is configured in cross-section in a shape selected from a group including rectangular, domal, triangular, rhomboidal and frustoconical.

6. A tubular medical device according to claim 1, wherein said body member is configured in a form selected from a group including a cylindrically-shaped tube, a rectangularly-shaped tube, a frustoconically-shaped tube and an elongated tube.

7. A tubular medical device according to claim 1, wherein said body member and said rib structure are of a unitary construction.

8. A tubular medical device according to claim 1, wherein said body member and said rib structure are fabricated from a group of materials including rubber, plastic, stainless steel, titanium, silicone and polyethylene.

9. A tubular medical device according to claim 8, wherein said body member and said rib structure are fabricated from one of the same material and different materials.

10. A tubular medical device according to claim 1, wherein said rib structure projects radially from said outer surface of said body member relative to the longitudinal axis.

11. A tympanostomy tube device adapted for insertion and temporary retention in an orifice formed in an eardrum of an ear structure of a living being to provide fluid communication between a middle ear cavity and an auditory canal of the ear structure, comprising:

a body member extending along a longitudinal axis and having an outer surface and an inner surface, said inner surface defining a hole extending longitudinally through said body member between opposite ends of said body member; and a rib structure in a form of a helix connected to said outer surface of said body member and projecting outwardly from said outer surface relative to the longitudinal axis in a manner whereby said rib structure and said outer surface define at least one channel oriented transversely to the longitudinal axis wherein said body member and said rib structure being sized to be received by the orifice formed in the eardrum.

12. A tymoanostomy tube device according to claim 11, wherein said rib structure extends from and between said opposite ends of said body member.

13. A tympanostomy tube device according to claim 11, wherein said rib structure is a plurality of rib elements, each of said r:-b elements disposed apart from one another to define the at least one channel therebetween and extending circumferentially around said outer surface of said body member, said plurality of rib elements disposed away from and between said opposite ends of said body member.

14. A tympanostomy tube device according to claim 11, wherein said body member is configured in a shape of a cylindrically-shaped tube and wherein said body member and said rib structure are of a unitary construction.

15. A tympanostomy tube device according to claim 14, wherein said body member and said rib structure are fabricated from a stiff yet resilient material selected from a group of materials including rubber, plastic, silicone and polyethylene.

16. A tympanostomy tube device according to claim 14, wherein said body member and said rib structure are fabricated from a rigid material selected from a group of materials including stainless steel and titanium.

* * * * *